(12) United States Patent
Ward et al.

(10) Patent No.: US 8,697,845 B2
(45) Date of Patent: Apr. 15, 2014

(54) ANTIBODIES SPECIFICALLY DIRECTED TO A SOLUBLE FORM OF CTLA-4

(75) Inventors: Frank James Ward, Aberdeen (GB); Robert Norman Barker, Aberdeen (GB); Lekh Nath Dahal, Aberdeen (GB)

(73) Assignee: The University Court of the University of Aberdeen, Aberdeen (GB)

( * ) Notice: Subject to any disclaimer, the term of this patent is extended or adjusted under 35 U.S.C. 154(b) by 0 days.

(21) Appl. No.: 13/203,418

(22) PCT Filed: Feb. 26, 2010

(86) PCT No.: PCT/GB2010/000351
§ 371 (c)(1),
(2), (4) Date: Jan. 4, 2012

(87) PCT Pub. No.: WO2010/097597
PCT Pub. Date: Sep. 2, 2010

(65) Prior Publication Data
US 2012/0107320 A1    May 3, 2012

(30) Foreign Application Priority Data

Feb. 26, 2009    (GB) .................................... 0903325.9

(51) Int. Cl.
*A61K 39/395*    (2006.01)
*C07K 16/00*    (2006.01)

(52) U.S. Cl.
USPC ...................................... 530/387.1; 424/130.1

(58) Field of Classification Search
None
See application file for complete search history.

(56) References Cited

U.S. PATENT DOCUMENTS

| 6,075,181 A * | 6/2000 | Kucherlapati et al. ........... 800/25 |
| 6,632,927 B2 * | 10/2003 | Adair et al. ................. 530/387.3 |
| 2003/0086932 A1 * | 5/2003 | Bluestone et al. .......... 424/178.1 |
| 2008/0242587 A1 * | 10/2008 | Kim et al. .......................... 514/2 |
| 2009/0017040 A1 * | 1/2009 | Pfeifer et al. ............... 424/152.1 |
| 2009/0252741 A1 * | 10/2009 | Liu et al. .................... 424/154.1 |
| 2011/0296546 A1 * | 12/2011 | Korman et al. .................. 800/18 |
| 2012/0045442 A1 * | 2/2012 | Hanson et al. .............. 424/142.1 |
| 2012/0100101 A1 * | 4/2012 | Nichol et al. ................. 424/85.2 |

FOREIGN PATENT DOCUMENTS

| WO | 2005/072340 A2 | 8/2005 |
| WO | 2006/059131 A1 | 6/2006 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Abcam clone 2C11 Data Sheet (2012), 1 page.*
Owens et al., Journal of Immunological Methods, 1994, 168: 149-165.*
Sequence Alignment (2012), 1 page.*
Clarkson et al., Nature, 1991, 352: 624-628.*
Portolano et al., J. Immunol., 1993, 150: 880-887.*
McKeever, Una, et al., "Immunization with Soluble BDC 2.5 T Cell Receptor-Immunoglobulin Chimeric Protein: Antibody Specificity and Protection of Nonobese Diabetic Mice Against Adoptive Transfer of Diabetes by Maternal Immunization," Journal Exp. Medicine, The Rockefeller University Press, Published Nov. 1, 1996, vol. 184, Issue Nov. 1996, pp. 1755-1768.
Oaks, Martin K., et al., "Cutting Edge: A Soluble Form of CTLA-4 in Patients with Autoimmune Thyroid Disease," The American Association of Immunologists, May 15, 2000, vol. 164, No. 10, pp. 5015-5018.
Pawlak, Edyta, et al., "The Soluble CTLA-4 Receptor: A New Marker in Autoimmune Diseases," Archive Immunology and Experimental Therapy, Jul. 2005, vol. 53, No. 4, pp. 336-341.
Riley, James L., et al., "The CD28 Family: a T-Cell Rheostat for Therapeutic Control of T-Cell Activation," The American Society of Hematology, Jan. 2005, vol. 105, No. 1, pp. 13-21.
Sato, S., et al., "Serum Soluble CTLA-4 Levels are Increased in Diffuse Cutaneous Systemic Sclerosis," Rheumatology. Jul. 20, 2004, vol. 43, No. 10, pp. 1261-1266.
Ward., F.J., et al., "Soluble CTLA-4 Responses—A Novel Mechanism for Regulatory T Cell Suppression?," Session 2: Regulatory T Cells: Ontogeny to Fundamental Mechanisms, Immunology, Blackwell Publishing, Oxford, GB, Mar. 2007, vol. 120, No. 1, p. 9.
Zhu, Naishuo, et al., "Expression of the Negative Co-Stimulatory Ligand sCD152 in the Yeast, *Pichia pastoris*, and its Regulation of Antigen Specific Immune Responses," International Immunopharmacology, Jan. 2004, vol. 4, No. 1, pp. 139-148.

* cited by examiner

*Primary Examiner* — Ilia Ouspenski
(74) *Attorney, Agent, or Firm* — Janet Sleath; Speckman Law Group PLLC

(57) ABSTRACT

The invention provides materials and methods relating to antibodies specific for a soluble form of CTLA-4 (sCLTA-4). Such antibodies have been shown to have a strong boosting effect on antigen-specific human immune responses.

18 Claims, 7 Drawing Sheets

Figure 2:
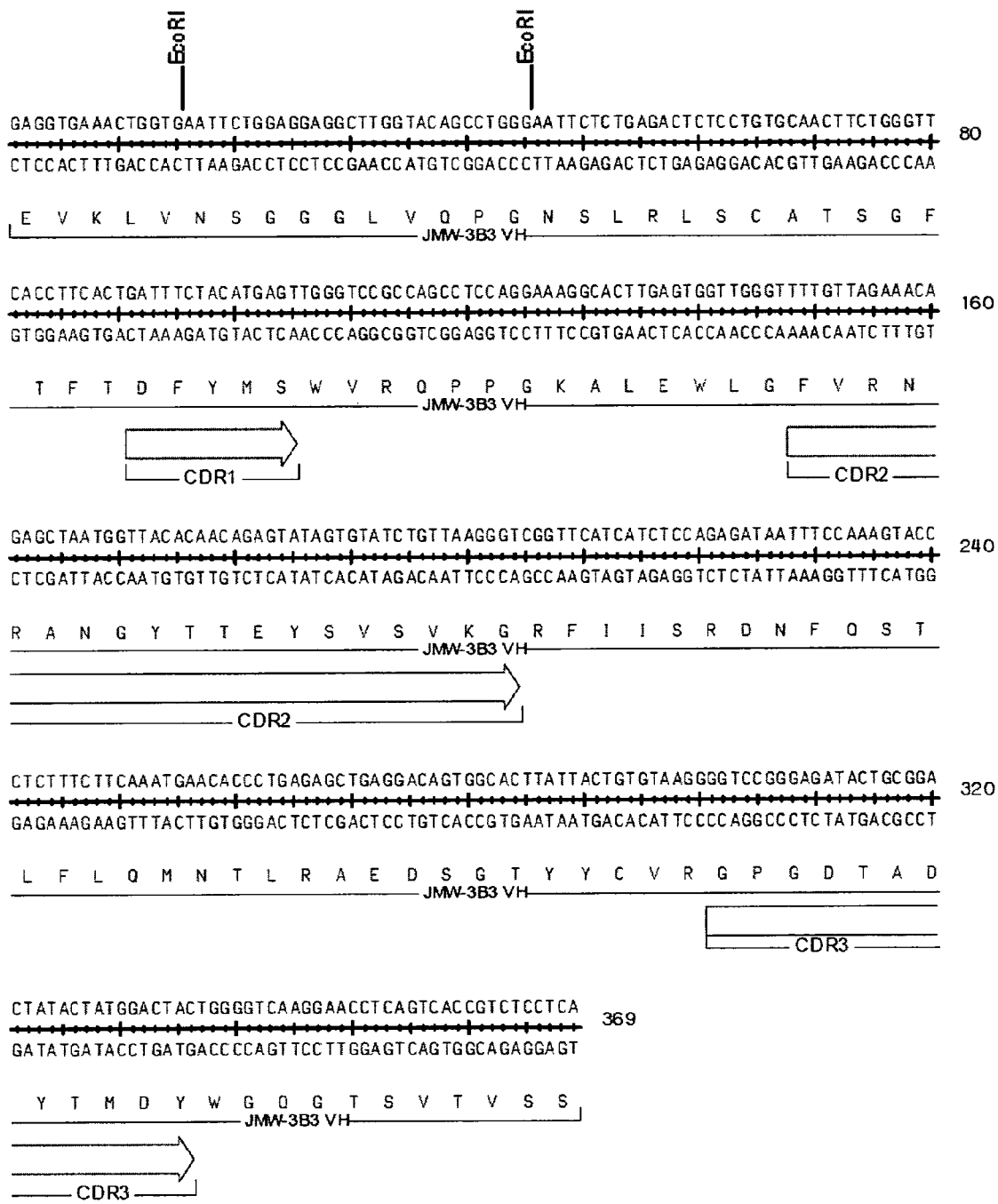

```
CAGGCTGTTGTGACTCAGGAATCTGCATTCACCACATCACCTGGTGGAACAGTCATACTCACTTGTCGCTCAAGTACTGG
                                                                                  80
GTCCGACAACACTGAGTCCTTAGACGTAAGTGGTGTAGTGGACCACCTTGTCAGTATGAGTGAACAGCGAGTTCATGACC

Q  A  V  V  T  Q  E  S  A  F  T  T  S  P  G  G  T  V  I  L  T  C  R  S  S  T  G
└────────────────────────────── JMW-3B3 V lambda ──────────────────────┘
                                                                        └─── CDR1 ──

GGCTGTTACAACTAATAACTATGCCAACTGGGTCCAAGAAAAACCAGATCATTTATTCACTGGTCTAATAGGTGGTACTA
                                                                                  160
CCGACAATGTTGATTATTGATACGGTTGACCCAGGTTCTTTTTGGTCTAGTAAATAAGTGACCAGATTATCCACCATGAT

A  V  T  T  N  N  Y  A  N  W  V  Q  E  K  P  D  H  L  F  T  G  L  I  G  G  T
──────────────────────────── JMW-3B3 V lambda ──────────────────────────────────
──────────────────────────▶
─────────── CDR1 ──────────┘                                              └ CDR2 ─

SacI
                     │
GCAACCGAGCTCCAGGTGTTCCTGTCAGATTCTCAGGCTCCCTGATTGGAGACAAGGCTGCCCTCACCATCACAGGGGCA
                                                                                  240
CGTTGGCTCGAGGTCCACAAGGACAGTCTAAGAGTCCGAGGGACTAACCTCTGTTCCGACGGGAGTGGTAGTGTCCCCGT

S  N  R  A  P  G  V  P  V  R  F  S  G  S  L  I  G  D  K  A  A  L  T  I  T  G  A
─────────────────────────── JMW-3B3 V lambda ──────────────────────────────────
──────▶
──── CDR2 ────┘

CAGACTGAGGATGATGGAATGTATTTCTGTGCTCTATGGTACACCACCCATTTTGTTTTCGGCGGTGGAACCAAGGTCAC
                                                                                  320
GTCTGACTCCTACTACCTTACATAAAGACACGAGATACCATGTGGTGGGTAAAACAAAAGCCGCCACCTTGGTTCCAGTG

Q  T  E  D  D  G  M  Y  F  C  A  L  W  Y  T  T  H  F  V  F  G  G  G  T  K  V  T
──────────────────────────── JMW-3B3 V lambda ──────────────────────────────────
                      ────────────────────────────────▶
                      └──────────── CDR3 ─────────────┘

TGTCCTAGGT
           330
ACAGGATCCA
```

Figure 1

SEQUENCE LISTING

```
<160> NUMBER OF SEQ ID NOS: 13

<210> SEQ ID NO 1
<211> LENGTH: 330
<212> TYPE: DNA
<213> ORGANISM: Mus musculus
<220> FEATURE:
<221> NAME/KEY: CDS
<222> LOCATION: (1)..(321)

<400> SEQUENCE: 1 cag gct gtt gtg act cag gaa tct gca ttc acc aca tca cct ggt gga      48
Gln Ala Val Val Thr Gln Glu Ser Ala Phe Thr Thr Ser Pro Gly Gly
1               5                  10                  15 aca gtc ata ctc act tgt cgc tca agt act ggg gct gtt aca act aat      96
Thr Val Ile Leu Thr Cys Arg Ser Ser Thr Gly Ala Val Thr Thr Asn
             20                  25                  30 aac tat gcc aac tgg gtc caa gaa aaa cca gat cat tta ttc act ggt     144
Asn Tyr Ala Asn Trp Val Gln Glu Lys Pro Asp His Leu Phe Thr Gly
         35                  40                  45 cta ata ggt ggt act agc aac cga gct cca ggt gtt cct gtc aga ttc     192
Leu Ile Gly Gly Thr Ser Asn Arg Ala Pro Gly Val Pro Val Arg Phe
     50                  55                  60 tca ggc tcc ctg att gga gac aag gct gcc ctc acc atc aca ggg gca     240
Ser Gly Ser Leu Ile Gly Asp Lys Ala Ala Leu Thr Ile Thr Gly Ala
65                  70                  75                  80 cag act gag gat gat gga atg tat ttc tgt gct cta tgg tac acc acc     288
Gln Thr Glu Asp Asp Gly Met Tyr Phe Cys Ala Leu Trp Tyr Thr Thr
                 85                  90                  95 cat ttt gtt ttc ggc ggt gga acc aag gtc act gtcctaggt                330
His Phe Val Phe Gly Gly Gly Thr Lys Val Thr
            100                 105

<210> SEQ ID NO 2
<211> LENGTH: 107
<212> TYPE: PRT
<213> ORGANISM: Mus musculus

<400> SEQUENCE: 2

Gln Ala Val Val Thr Gln Glu Ser Ala Phe Thr Thr Ser Pro Gly Gly
1               5                  10                  15

Thr Val Ile Leu Thr Cys Arg Ser Ser Thr Gly Ala Val Thr Thr Asn
             20                  25                  30

Asn Tyr Ala Asn Trp Val Gln Glu Lys Pro Asp His Leu Phe Thr Gly
         35                  40                  45

Leu Ile Gly Gly Thr Ser Asn Arg Ala Pro Gly Val Pro Val Arg Phe
     50                  55                  60
```

```
Ser Gly Ser Leu Ile Gly Asp Lys Ala Ala Leu Thr Ile Thr Gly Ala
 65                  70                  75                  80

Gln Thr Glu Asp Asp Gly Met Tyr Phe Cys Ala Leu Trp Tyr Thr Thr
                 85                  90                  95

His Phe Val Phe Gly Gly Gly Thr Lys Val Thr
            100                 105
```

<210> SEQ ID NO 3
<211> LENGTH: 369
<212> TYPE: DNA
<213> ORGANISM: Mus musculus
<220> FEATURE:
<221> NAME/KEY: CDS
<222> LOCATION: (1)..(369)

<400> SEQUENCE: 3

```
gag gtg aaa ctg gtg aat tct gga gga ggc ttg gta cag cct ggg aat        48
Glu Val Lys Leu Val Asn Ser Gly Gly Gly Leu Val Gln Pro Gly Asn
  1               5                  10                  15 tct ctg aga ctc tcc tgt gca act tct ggg ttc acc ttc act gat ttc        96
Ser Leu Arg Leu Ser Cys Ala Thr Ser Gly Phe Thr Phe Thr Asp Phe
                 20                  25                  30 tac atg agt tgg gtc cgc cag cct cca gga aag gca ctt gag tgg ttg       144
Tyr Met Ser Trp Val Arg Gln Pro Pro Gly Lys Ala Leu Glu Trp Leu
             35                  40                  45 ggt ttt gtt aga aac aga gct aat ggt tac aca aca gag tat agt gta       192
Gly Phe Val Arg Asn Arg Ala Asn Gly Tyr Thr Thr Glu Tyr Ser Val
         50                  55                  60 tct gtt aag ggt cgg ttc atc atc tcc aga gat aat ttc caa agt acc       240
Ser Val Lys Gly Arg Phe Ile Ile Ser Arg Asp Asn Phe Gln Ser Thr
 65                  70                  75                  80 ctc ttt ctt caa atg aac acc ctg aga gct gag gac agt ggc act tat       288
Leu Phe Leu Gln Met Asn Thr Leu Arg Ala Glu Asp Ser Gly Thr Tyr
                 85                  90                  95 tac tgt gta agg ggt ccg gga gat act gcg gac tat act atg gac tac       336
Tyr Cys Val Arg Gly Pro Gly Asp Thr Ala Asp Tyr Thr Met Asp Tyr
            100                 105                 110 tgg ggt caa gga acc tca gtc acc gtc tcc tca                           369
Trp Gly Gln Gly Thr Ser Val Thr Val Ser Ser
            115                 120
```

<210> SEQ ID NO 4
<211> LENGTH: 123
<212> TYPE: PRT
<213> ORGANISM: Mus musculus

<400> SEQUENCE: 4

```
Glu Val Lys Leu Val Asn Ser Gly Gly Gly Leu Val Gln Pro Gly Asn
  1               5                  10                  15

Ser Leu Arg Leu Ser Cys Ala Thr Ser Gly Phe Thr Phe Thr Asp Phe
                 20                  25                  30

Tyr Met Ser Trp Val Arg Gln Pro Pro Gly Lys Ala Leu Glu Trp Leu
             35                  40                  45

Gly Phe Val Arg Asn Arg Ala Asn Gly Tyr Thr Thr Glu Tyr Ser Val
         50                  55                  60

Ser Val Lys Gly Arg Phe Ile Ile Ser Arg Asp Asn Phe Gln Ser Thr
 65                  70                  75                  80

Leu Phe Leu Gln Met Asn Thr Leu Arg Ala Glu Asp Ser Gly Thr Tyr
                 85                  90                  95

Tyr Cys Val Arg Gly Pro Gly Asp Thr Ala Asp Tyr Thr Met Asp Tyr
```

```
                  100                 105                 110
Trp Gly Gln Gly Thr Ser Val Thr Val Ser Ser
        115                 120

<210> SEQ ID NO 5
<211> LENGTH: 5
<212> TYPE: PRT
<213> ORGANISM: Mus musculus

<400> SEQUENCE: 5

Asp Phe Tyr Met Ser
1               5

<210> SEQ ID NO 6
<211> LENGTH: 19
<212> TYPE: PRT
<213> ORGANISM: Mus musculus

<400> SEQUENCE: 6

Phe Val Arg Asn Arg Ala Asn Gly Tyr Thr Thr Glu Tyr Ser Val Ser
1               5                   10                  15

Val Lys Gly

<210> SEQ ID NO 7
<211> LENGTH: 12
<212> TYPE: PRT
<213> ORGANISM: Mus musculus

<400> SEQUENCE: 7

Gly Pro Gly Asp Thr Ala Asp Tyr Thr Met Asp Tyr
1               5                   10

<210> SEQ ID NO 8
<211> LENGTH: 14
<212> TYPE: PRT
<213> ORGANISM: Mus musculus

<400> SEQUENCE: 8

Arg Ser Ser Thr Gly Ala Val Thr Thr Asn Asn Tyr Ala Asn
1               5                   10

<210> SEQ ID NO 9
<211> LENGTH: 7
<212> TYPE: PRT
<213> ORGANISM: Mus musculus

<400> SEQUENCE: 9

Gly Thr Ser Asn Arg Ala Pro
1               5

<210> SEQ ID NO 10
<211> LENGTH: 9
<212> TYPE: PRT
<213> ORGANISM: Mus musculus

<400> SEQUENCE: 10

Ala Leu Trp Tyr Thr Thr His Phe Val
1               5

<210> SEQ ID NO 11
<211> LENGTH: 22
<212> TYPE: PRT
<213> ORGANISM: Homo sapiens

<400> SEQUENCE: 11
```

```
Ala Lys Glu Lys Lys Pro Ser Tyr Asn Arg Gly Leu Cys Glu Asn Ala
1               5                   10                  15

Pro Asn Arg Ala Arg Met
                20

<210> SEQ ID NO 12
<211> LENGTH: 369
<212> TYPE: DNA
<213> ORGANISM: Mus musculus

<400> SEQUENCE: 12
tgaggagacg gtgactgagg ttccttgacc ccagtagtcc atagtatagt ccgcagtatc      60
tcccggaccc cttacacagt aataagtgcc actgtcctca gctctcaggg tgttcatttg     120
aagaaagagg gtactttgga aattatctct ggagatgatg aaccgaccct taacagatac     180
actatactct gttgtgtaac cattagctct gtttctaaca aaaccaacc actcaagtgc      240 ctttcctgga ggctggcgga cccaactcat gtagaaatca gtgaaggtga acccagaagt     300
tgcacaggag agtctcagag aattcccagg ctgtaccaag cctcctccag aattcaccag     360
tttcacctc                                                             369

<210> SEQ ID NO 13
<211> LENGTH: 330
<212> TYPE: DNA
<213> ORGANISM: Mus musculus

<400> SEQUENCE: 13
acctaggaca gtgaccttgg ttccaccgcc gaaaacaaaa tgggtggtgt accatagagc      60
acagaaatac attccatcat cctcagtctg tgccctgtg atggtgaggg cagccttgtc     120
tccaatcagg gagcctgaga atctgacagg aacacctgga gctcggttgc tagtaccacc    180
tattagacca gtgaataaat gatctggttt tccttggacc cagttggcat agttattagt    240
tgtaacagcc ccagtacttg agcgacaagt gagtatgact gttccaccag gtgatgtggt   300
gaatgcagat tcctgagtca caacagcctg                                    330
```

ANTIBODIES SPECIFICALLY DIRECTED TO A SOLUBLE FORM OF CTLA-4

CROSS-REFERENCE TO RELATED APPLICATIONS

This application is a U.S. National Stage filing under 35 U.S.C. §371 of, and claims priority to, PCT/GB2010/000357, filed Feb. 26, 2010, which claims priority to British Application No. 0903325.9, filed Feb. 26, 2009.

TECHNICAL FIELD

The present invention relates to antibody molecules, including antibodies and functional parts thereof, specifically directed to the human soluble form of cytotoxic T-lymphocyte antigen 4 (CTLA-4), and methods and materials related thereto.

SEQUENCE LISTING

The present application includes a Sequence Listing in electronic format as a txt file titled "6680862.txt," which was created on Nov. 3, 2011 and which has a size of 8,423 bytes. The contents of txt file "6680862.txt" are incorporated by reference herein.

BACKGROUND ART

The ability to modulate the adaptive immune response in patients offers the potential for powerful targeted therapies with improved safety compared with currently available conventional drugs. Methods aimed at either boosting or suppressing T cell responses could be successfully exploited as therapies in a number of diseases. This is because T cells form an important component of the adaptive immune system mediating both specificity and memory for a pathogenic challenge, providing a focus for developing highly selective therapies to replace current blanket therapies that affect the immune system as a whole and control rather than cure disease.

Full activation of T cells requires stimulation through the T cell antigen receptor and additional signalling via co-stimulatory molecules displayed on the cell surface of T cells, primarily the CD28 receptor (1-3). The ligands for CD28 are CD80 (B7.1) and CD86 (B7.2), displayed by cells such as dendritic cells, macrophages and B cells that also present antigen to the receptive T cell (4,5). Engagement of CD28 by CD80 or CD86 stimulates signalling pathways that stabilise and amplify the antigen-specific T cell response. This is characterised by increased T cell production of the cytokine IL-2, expression of proteins that suppress apoptosis ($Bcl-X_L$), and secretion of effector cytokines that amplify the antigen-specific immune response.

CTLA-4 is a structural homologue of CD28, both are members of the immunoglobulin superfamily, share approximately 30% amino acid sequence homology, and in humans, are located in the same region of chromosome 2 (6-8). Notably, both retain sequence motifs important for binding CD80/CD86. However, CTLA-4 is widely accepted as a receptor with opposing effects on T cell activity compared with CD28, delivering inhibitory rather than stimulatory signals to activated T cells. It is generally acknowledged to be a counter-receptor that can attenuate the intensity of the immune response prosecuted by the activated T cell on which it is displayed (9,10). It is also widely accepted that $CD4^+$ regulatory T cells constitutively express the molecule on their cell-surface, whereas other effector T cell subsets e.g., $CD4^+$ Th1 T cells, only express it following activation (11-13). There is further evidence that the molecule participates in Treg function and thus CTLA-4 may be involved in regulating the immune response both by modulating the intrinsic activity of the cell that expresses it and by inhibiting other activated T cells during an immune response (14-18).

Attempts to delineate the role of CTLA-4 in T cell stimulation demonstrated that it is important as an inhibitory regulator of T cells. First, mice deficient for the CTLA-4 gene die 3-5 weeks after birth from a massive lymphoproliferative disorder in which activated T cell blasts accumulate rapidly in lymphatic tissues and progress to infiltrate other organs and tissues of the body (19,20). This provides evidence that CTLA-4 has a role both in limiting the activation status of T cells and maintaining T cell homeostasis. Further, studies with antibodies specific for CTLA-4 have been used to evaluate its role in purified T cell populations and found that antibody cross-linking of CTLA-4 on the cell surface inhibits T cell proliferation and IL-2 production (21-24). These effects directly opposed the stimulatory effects mediated by CD28 and so it is likely that the CD28 and CTLA-4 co-stimulation molecules combine to modulate T cell antigen receptor stimulation by delivering stimulatory and inhibitory signals respectively.

Antibody blockade of CTLA-4 has been widely used to demonstrate that inhibition of CTLA-4 function enhances T cell activity in a range of disease situations, including cancer, infection and other immune-related scenarios. In cancer, antibody blockade of CTLA-4 function has been established as a potentially viable method of establishing powerful anti-tumour T cell responses (25-31; see also U.S. Pat. No. 6,984,720 assigned to Medarex, Inc.). The first experiments were conducted in murine models of cancer. Blockade of CTLA-4 enhanced anti-tumor T cell immune responses leading to successful reduction and abolition of tumours. Blockade of CTLA-4 has been performed in cancer models using antibody alone or in combination with a vaccine specific to the cancer. It seems that the natural immunogenicity of the particular tumour is a determining factor of whether CTLA-4 blockade alone, or blockade in combination with a vaccine or other immune activator is sufficient to generate a successful anti-tumour immune response. Initial studies of CTLA-4 blockade in murine models of cancer have led to similar studies in humans and at least two monoclonal antibodies specific for human CTLA-4 have been extensively studied in clinical trials aimed at treating a diverse range of cancers (31).

In connection with infection, antibody blockade of CTLA-4 function demonstrated greatly enhanced immune responses including anti-parasitic, anti-bacterial and anti-viral responses enhancing a spectrum of immunity including increased antigen specific antibody, and Th1/Th2 T helper cell responses (32-36). Antibody blockade of CTLA-4 also enhances autoimmune responses (37).

Most research concerning CTLA-4 has focussed on the receptor form of the molecule but there are alternative genetic isoforms, which in protein form do not reside on the cell surface of T cells (reviewed by Teft et al. (2006) (38)).

The full length membrane-bound isoform of CTLA-4 is encoded in humans by four exons (1-4) on chromosome 2, but there are other mRNA transcripts including one that generates a secretable soluble form of CTLA-4 (sCTLA-4) (39,40). This alternatively spliced transcript is missing exon 3, corresponding to the transmembrane domain of full-length CTLA-4, and a reading frame shift of exon 4 replaces the cytoplasmic tail sequence with a different C-terminal amino acid sequence of no known function. Like full-length CTLA-4, sCTLA-4 has the capacity to bind B7.1/B7.2 co-stimulator ligands on APC but its role as a regulator of antigen-specific immune responses has not been evaluated. Initial studies indicated that resting T cells are the primary source of sCTLA-4, which after non-specific activation with anti-CD3 mAb, rapidly switch to producing the full-length isoform to regulate the immune response.

The Oaks and Hallett (43) describe the production of a rabbit polyclonal antiserum to the C terminal region of sCTLA-4. The antiserum was used in Western blots to detect presence of the sCTLA-4 protein. It was not used in any functional assays.

Single nucleotide polymorphisms (SNP) within the CTLA-4 gene locus have been associated with susceptibility for autoimmune disease. A powerful population analysis of a CTLA-4 associated SNP (CT60) found that a particular haplotype (homozygous g/g) correlated with increased susceptibility for Graves' disease, autoimmune hypothyroidism and type 1 diabetes (41). The SNP is located downstream of the 4 CTLA-4 encoding exons and subsequent analysis indicated that the susceptibility SNP is influential upon CTLA-4 by determining a relative decrease in the amount of sCTLA-4 protein produced. Expression levels of full length CTLA-4 were not affected. These data provided evidence that sCTLA-4 may in fact have a role in regulating the immune system.

WO2005/072340 describes variants of the CTLA-4 receptor and soluble CTLA-4 molecules.

Other CTLA-4 alternative isoforms include liCTLA-4, present in rodents but not humans, where the alternative transcript lacks exon 2, and another encoded only by the exons 1 and 4 (38). This latter transcript, present in humans, has no reported function at present.

DISCLOSURE OF THE INVENTION

The present inventors have provided an monoclonal antibody, termed herein JMW-3B3, that is specific for the soluble form of CTLA-4 hence does not bind to other isoforms or recombinant CTLA-4 proteins since they lack the required selected epitope.

By contrast, current antibodies which bind CTLA-4 bind both isoforms, typically identifying epitopes in protein regions encoded by exon 2.

In addition to the other utilities described below, the sCTLA-4 specific JMW-3B3 antibody has a strong boosting effect on antigen-specific human immune responses and particularly antigen-specific T lymphocytic cells (T cells). This activity was not predictable from the prior art. Specifically, in previous work in the art, sCTLA-4 was generally considered to be produced by resting T cells and not to be an active component of an immune response. This was consistent with the view that sCTLA-4 was secreted in monomeric form, and on that basis would have been considered as unlikely to have the functional potency required to regulate immune responses (by contrast studies of full-length CTLA-4 revealed that it is displayed on cell surfaces in dimeric form and that dimerism plays a major role in its function (42). Equally, artificial recombinant CTLA4-Ig is more potent in dimeric form (8)).

Studies with mAb JMW-3B3 have revealed that sCTLA-4, in contrast to those assumptions, is likely to be dimeric in functional form. Without wishing to be bound by theory, this may explain why blockade of its function has such strong and unexpected effects on antigen-specific immune responses in terms of cell proliferation and effector cytokine production.

Nucleotide sequences and amino acid sequences that comprise the mAb JMW-3B3 antibody variable regions including the framework (FR) and complementarity determining region (CDRs) sequences, specifically those that span FR1 through CDR1, FR2, CDR2, FR3, CDR3 and FR4 for both variable heavy (VH) and variable light chain (VL) regions, are provided (see FIGS. 1 and 2).

As described in more detail below, preferred embodiments of the present invention employ the antibody VH and/or VL domains of JMW-3B3 or fragments or variants thereof. Further preferred embodiments employ one or more complementarity determining regions (CDRs) of the JMW-3B3 heavy chain variable (VH) and/or light chain variable (VL) domains, especially VH JMW-3B3 (or variants of any of these) in other antibody framework regions.

Some aspects and embodiments of the invention will now be discussed in more detail.

In one aspect, the present invention provides an antibody molecule which binds specifically to sCTLA-4.

As antibodies can be modified in a number of ways, the term "antibody molecule" should be construed as covering any antibody molecule or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Preferred antibody molecules are monoclonal antibodies such as JMW-3B3 according to the invention including any functionally equivalent antibodies thereto and functional parts thereof. Examples of such equivalents and parts are described in more detail hereinafter.

"Specifically" in the context of the invention this means the ability to bind to sCTLA-4, but shows essentially no binding to the other major form of CTLA-4 on the surfaces of lymphocytes. The antibody molecules of the invention may likewise show essentially no binding to the artificial recombinant form of CTLA-4 termed "CTLA4-Ig".

By "essentially no binding" a binding is meant, which is at least about 85%, particularly at least about 90%, more particularly at least about 95%, even more particularly at least about 98%, but especially at least about 99% and up to 100% less than the binding to sCTLA4.

Figure 5:
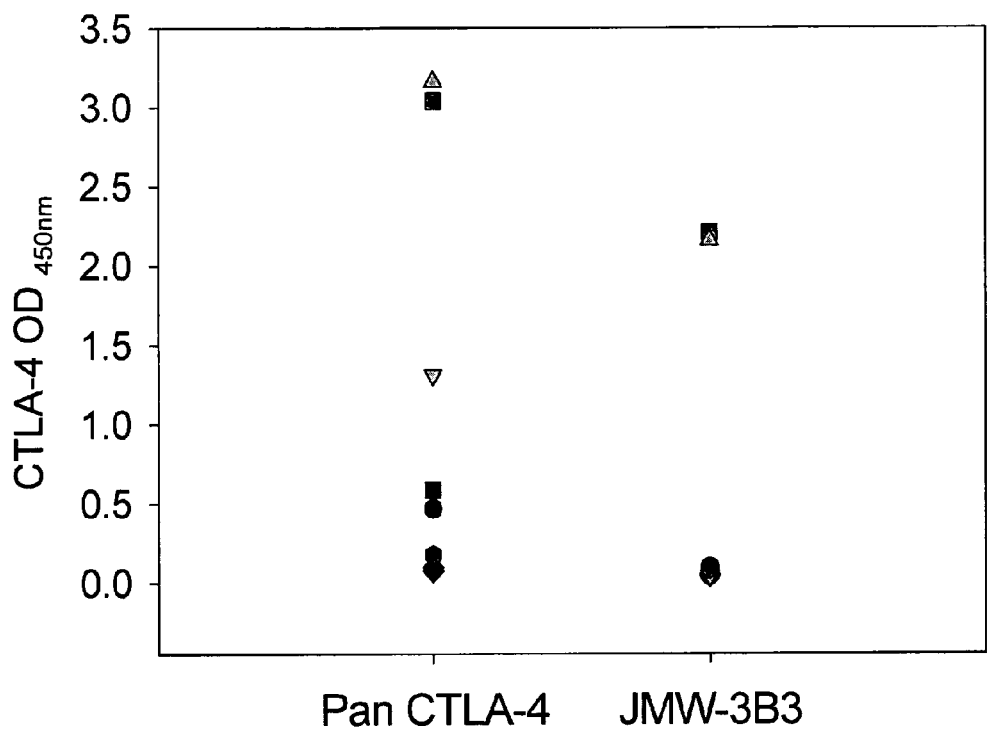

Typically, specificity may be determined by means of a binding assay such as ELISA employing a panel of antigens, wherein it can be demonstrated that an antibody molecule according to the present invention will specifically recognise sCTLA-4 but not CTLA4 (see FIG. 5). As an alternative, a sensor such as a Biacore sensor may be used to compare or quantify binding.

In one aspect the invention provides an antibody molecule which binds an epitope within the amino acid sequence:

(SEQ ID NO: 11)
AKEKKPSYNRGLCENAPNRARM.

This sequence is part of the sCTLA4 C-terminal protein sequence ($A_{116}$-$M_{137}$), and differs from that of the CTLA-4 isoform commonly detected on the surface of human T cells.

Thus an antibody molecule according to the invention may be one which competes for binding to sCTLA4 (and in particular to an epitope in SEQ ID NO: 11) with any antibody molecule which both binds the antigen and comprises an antibody molecule, VH and/or VL domain disclosed herein, or VH CDR3 disclosed herein, or variant of any of these.

Competition between antibody molecules may be assayed easily in vitro, for example using ELISA and/or by tagging a specific reporter molecule to one antibody molecule which can be detected in the presence of other untagged antibody molecule(s), to enable identification of antibody molecules which bind the same epitope or an overlapping epitope.

Thus a further aspect of the present invention provides an antibody molecule comprising a human antibody antigen-binding site which competes with JMW-3B3 for binding to sCTLA-4 (for example to an epitope in SEQ ID NO: 11) and which likewise does not bind CTLA-4 on the surfaces of lymphocytes.

In the light of the disclosure herein, antibodies specific for sCTLA-4 and which may compete with JMW-3B3 for binding to the same or nearby sCTLA-4 epitope can be readily provided. For example, a method may include bringing into contact a library of antibody molecules and said epitope, and selecting one or more specific antibody molecules of the library able to bind said epitope.

The library may be displayed on the surface of bacteriophage particles, each particle containing nucleic acid encoding the antibody VH variable domain displayed on its surface, and optionally also a displayed VL domain if present.

Following selection of specific antibody molecules able to bind the epitope and displayed on bacteriophage particles, nucleic acid may be taken from a bacteriophage particle displaying a said selected specific antibody molecule. Such nucleic acid may be used in subsequent production of a specific antibody molecule or an antibody VH variable domain (optionally an antibody VL variable domain) by expression from nucleic acid with the sequence of nucleic acid taken from a bacteriophage particle displaying a said selected specific antibody molecule.

Ability to specifically bind sCTLA-4 may be further tested, also ability to compete with JMW-3B3 for binding to sCTLA-4. Ability to antagonise action of sCTLA-4 in certain contexts may also be tested, as discussed further below.

An antibody molecule according to the present invention may bind sCTLA-4 with the affinity of JMW-3B3.

Thus the present invention further extends to an antibody molecule which competes for binding to sCTLA-4 with any antibody molecule which both binds sCTLA-4 and comprises a V domain including a CDR with amino acid substantially as set out herein or a V domain with amino acid sequence substantially as set out herein. Competition between antibody molecules may be assayed easily in vitro, for example by tagging a reporter molecule to one antibody molecule which can be detected in the presence of other untagged antibody molecule(s), to enable identification of antibody molecules which bind the same epitope or an overlapping epitope. Competition may be determined for example using ELISA or flow cytometry.

In testing for competition a peptide fragment of sCTLA-4 may be employed, especially a peptide including the epitope of interest. A peptide having the epitope sequence plus one or more amino acids at either end may be used. Such a peptide may be said to "consist essentially" of the specified sequence. Antibody molecules according to the present invention may be such that their binding for sCTLA-4 is inhibited by a peptide with or including the sequence given. In testing for this, a peptide with either sequence plus one or more amino acids may be used.

As noted above, preferred antibody molecules are monoclonal antibodies such as JMW-3B3 according or functionally equivalent antibodies or functional parts thereof.

In a preferred embodiment, the antibody molecule comprises the JMW-3B3 VH domain (SEQ ID NO: 4) and/or the JMW-3B3 VL domain (SEQ ID NO: 2).

Generally, a VH domain is paired with a VL domain to provide an antibody antigen binding site, although as discussed further below a VH domain alone may be used to bind antigen.

In one preferred embodiment, the JMW-3B3 VH domain (SEQ ID NO: 4) is paired with the JMW-3B3 VL domain (SEQ ID NO: 2), so that an antibody antigen binding site is formed comprising both the JMW-3B3 VH and VL domains. In other embodiments, the JMW-3B3 VH is paired with a VL domain other than the JMW-3B3 VL. Light-chain promiscuity is well established in the art.

One or more CDR's may be taken from the JMW-3B3 VH or VL domain and incorporated into a suitable framework. This is discussed further below. JMW-3B3 VH CDR's 1, 2 and 3 are shown in SEQ ID Nos 5, 6 and 7, respectively. JMW-3B3 VL CDR's 1, 2 and 3 are shown in SEQ ID Nos 8, 9 and 10, respectively.

Variants of the VH and VL domains of which the sequences are set out herein and which can be employed in antibody molecules for sCTLA-4 can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention. Particular variants may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDR's.

Preferred substitutions are conservative substitutions.

Thus one aspect of the invention provides a method for obtaining an antibody antigen-binding domain specific for a sCTLA-4 epitope within AKEKKPSYNRGLCENAPN-RARM, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify an antibody molecule or an antibody antigen binding domain specific for sCTLA-4. Said VL domain may have an amino acid sequence which is substantially as set out herein.

An analogous method may be employed in which one or more sequence variants of a VL domain disclosed herein are combined with one or more VH domains.

In one embodiment, the invention relates to a VL region exhibiting an amino acid sequence that is 85%, 86%, 87%, 88%, 89%, 90%, 91%, 92%, 93%, 94%, 95%, 96%, 97%, 98% or 99% identical to the sequence given in SEQ ID NO: 2 or a functional part thereof comprising at least one, particularly at least two, more particularly at least 3 of the light chain CDRs, but especially all CDRs embedded in their natural framework regions.

In one embodiment, the invention relates to a VH region exhibiting an amino acid sequence that is 85%, 86%, 87%, 88%, 89%, 90%, 91%, 92%, 93%, 94%, 95%, 96%, 97%, 98% or 99% identical to the sequence given in SEQ ID NO: 4, or a functional part thereof comprising at least one, particularly at least two, more particularly at least 3 of the heavy chain CDRs, but especially all CDRs embedded in their natural framework regions.

A further aspect of the invention provides an antibody molecule such as a monoclonal antibody including any functionally equivalent antibody or functional parts thereof according to the present invention and as described herein wherein said antibody comprises a VL or VH domain as described herein.

A further aspect of the invention provides a method of preparing an antibody molecule specific for sCTLA-4, which method comprises:
(a) providing a starting repertoire of nucleic acids encoding a VH domain which either include a CDR3 to be replaced or lack a CDR3 encoding region;
(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
(c) expressing the nucleic acids of said product repertoire;
(d) selecting an antibody molecule specific for sCTLA-4; and
(e) recovering said specific antibody molecule or nucleic acid encoding it.

Again, an analogous method may be employed in which a VL CDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for antibody molecules specific for sCTLA-4.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific antibody molecules of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Antibody molecules of the present invention include antibody molecules and other immunoglobulins whether natural or partly or wholly synthetically produced. The term covers any polypeptide or protein comprising an antibody binding domain. Specifically includes are antibody fragments which comprise an antigen binding domain are such as Fab, scFv, Fv, dAb, Fd; and diabodies. These things are discussed in more detail below.

Although in a preferred aspect of the invention specific antibody molecules comprising a pair of VH and VL domains are preferred, single binding domains based on either VH or VL domain sequences form further aspects of the invention. It is known that single immunoglobulin domains, especially VH domains, are capable of binding target antigens in a specific manner.

Thus in other aspects of the invention an antibody VH variable domain with the amino acid sequence of an antibody VH variable domain of an antibody molecule of the invention may be provided in isolated form, as may an antibody molecule comprising such a VH domain.

In the case of either of the single chain binding domains, these domains may also be used to screen for complementary domains capable of forming a two-domain antibody molecule able to bind sCTLA-4.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain antibody molecule is selected in accordance with phage display techniques such as those described in that reference. This technique is also disclosed in Marks et al, ibid.

Antibody molecules of the present invention may further comprise antibody constant regions or parts thereof. For example, a VL domain may be attached at its C-terminal end to antibody light chain constant domains including human Cκ or Cλ chains, preferably Cκ chains. Similarly, an antibody molecule based on a VH domain may be attached at its C-terminal end to all or part of an immunoglobulin heavy chain derived from any antibody isotype, e.g. IgG, IgA, IgE and IgM and any of the isotype sub-classes. Fc regions such as Δnab and Δnac as disclosed in WO99/58572 may be employed.

WO 94/25591 discusses the utility of framework regions of immunoglobulins from Camelidae in the provision of single chain binding domains. On other embodiments the antibody or framework regions may be derived from the immunoglobulin of a cartilaginous fish such as a shark (see e.g. J Immunol. 2008 Jun. 1; 180(11):7461-70)

An antibody molecule in some preferred embodiments of the invention is a monomeric fragment, such as F(ab) or scFv. Such antibody fragments may have the advantage of a relatively short half life.

In addition to antibody sequences, an antibody molecule according to the present invention may comprise other amino acids, e.g. forming a peptide or polypeptide, such as a folded domain, or to impart to the molecule another functional characteristic (e.g. improved half-life) in addition to ability to specifically bind sCTLA4.

In one embodiment, antibody molecules of the invention may be modified with hydrophilic moieties, particularly a polyethylene glycol (PEG) moiety, wherein said hydrophilic moiety is covalently bound to each terminus through an amino acid such as, for example, lysine or any other suitable amino acid or amino acid analogue capable of serving as a linker molecule; and isolating the antibody.

Those skilled in the art are aware of numerous approaches to chemically conjugating molecules to proteins. When the antibody molecule is for pharmaceutical use the conjugate bond is preferably stable in circulation but labile once the conjugate is sequestered intracellularly.

Thus, for example, antibody molecules of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin. Preferably the labels include fluorescent labels such as FITC.

The present invention further provides an isolated nucleic acid encoding an antibody molecule of the present invention. Nucleic acid includes DNA and RNA. In a preferred aspect, the present invention provides a nucleic acid which codes for a CDR, VH or VL domain of the invention as defined herein, and methods of preparing an antibody molecule, a VH domain and/or a VL domain of the invention, which comprise expressing said nucleic acid under conditions to bring about production of said antibody molecule, VH domain and/or VL domain, and recovering it.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR, VH or VL domain, or antibody molecule as provided itself forms an aspect of the present invention, as does a method of production of the encoded product, which method comprises expression from nucleic acid which encodes it. Expression may conveniently be achieved by culturing under appropriate conditions recombinant host cells containing the nucleic acid. Following production by expression a VH or VL domain, or antibody molecule may be isolated and/or purified using any suitable technique, then used as appropriate.

Antibody molecules, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells, YB2/0 rat myeloma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of an antibody molecule, see for recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. *Molecular Cloning: a Laboratory Manual:* 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992.

Thus, a further aspect of the present invention provides a host cell containing or transformed with nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express an antibody molecule or polypeptide as above.

Thus, for example, the present invention provides in various aspects:

A nucleic acid comprising a nucleotide sequence encoding a VL region exhibiting an amino acid sequence that is 85%, 86%, 87%, 88%, 89%, 90%, 91%, 92%, 93%, 94%, 95%, 96%, 97%, 98% or 99% identical to the sequence given in SEQ ID NO: 2 or a functional part thereof comprising at least one, particularly at least two, more particularly at least 3 of the light chain CDRs, but especially all CDRs embedded in their natural framework regions.

A nucleic acid comprising a nucleotide sequence encoding a VL region exhibiting an amino acid sequence that is 85%, 86%, 87%, 88%, 89%, 90%, 91%, 92%, 93%, 94%, 95%, 96%, 97%, 98% or 99% identical to the sequence given in SEQ ID NO: 4, or a functional part thereof comprising at least one, particularly at least two, more particularly at least 3 of the heavy chain CDRs, but especially all CDRs embedded in their natural framework regions.

Nucleic acid, generally isolated, encoding an antibody VH variable domain (SEQ ID NO: 3) and/or VL variable domain (SEQ ID NO: 1) disclosed herein.

Another aspect of the present invention provides nucleic acid, generally isolated, encoding a VH CDR or VL CDR sequence disclosed herein, especially a VH CDR selected from SEQ ID Nos 5, 6 and 7 or a VL CDR selected from SEQ ID Nos 8, 9 and 10, most preferably JMW-3B3 VH CDR3 (SEQ ID NO: 7).

A method of production of an antibody VH variable domain, the method including causing expression from encoding nucleic acid. Such a method may comprise culturing host cells under conditions for production of said antibody VH variable domain.

Analogous methods for production of VL variable domains and antibody molecules comprising a VH and/or VL domain.

A method of production may comprise a step of isolation and/or purification of the product.

A method of production may comprise formulating the product into a composition including at least one additional component, such as a pharmaceutically acceptable excipient.

The sCTLA-4 specific JMW-3B3 antibody has a strong boosting effect on antigen-specific human immune responses and particularly antigen-specific T lymphocytic cells (T cells). This activity was not predictable from the prior art.

The ability of an antibody molecule specific for the soluble CTLA-4 isoform to boost the T cell response to immunogenic or antigenic challenge in a selective targeted way, without affecting cell surface, full length CTLA-4 function, has considerable utility and can be exploited in a number of disease situations.

Thus antibody molecules according to present invention may be capable of enhancing antigen-specific T lymphocytic cell responses, for example by promoting proliferation of antigen-specific cells and production of cytokine molecules involved in driving these antigen-specific immune responses.

To measure such responses, a typical assay might comprise purified peripheral blood mononuclear cells (PBMC) incubated for 5 days at 37° C., 5% $CO_2$, in the presence or absence of antigen, and either JMW-3B3 anti-sCTLA-4 antibody or a non-specific matched isotype control antibody. Following a period during which an immune response is allowed to develop in vitro (typically 4-5 days), boosting of the immune response by JMW-3B3 can be determined by measuring effector cytokines by ELISA, e.g., interferon-γ.

"Immunogenic or antigenic challenge" is defined as any challenge that promotes an adaptive immune response including microbial, viral or parasitic pathogens, cancer cells, or derived protein immunogens and antigens thereof.

Antibody molecules according to the invention, for instance having the antigen-specific boosting effect described above, may be used in a method of treatment or diagnosis of the human or animal body, such as a method of treatment (which may include prophylactic treatment) of a disease or disorder in a human patient which comprises administering to said patient an effective amount of an antibody molecule of the invention. Conditions treatable in accordance with the present invention include those discussed elsewhere herein.

Further aspects of the invention provide methods of treatment comprising administration of an antibody molecule as provided, pharmaceutical compositions comprising such an antibody molecule, and use of such an antibody molecule in the manufacture of a medicament for administration, for example in a method of making a medicament or pharmaceutical composition comprising formulating the antibody molecule with a pharmaceutically acceptable excipient.

Thus in different aspects of the invention, functional blockade of sCTLA-4 using antibody molecules of the invention selective for sCTLA-4 can be used to enhance antigen-specific immune responses, for example as follows:

Enhancement of immune responses against immunogenic tumours.

Enhancement of anti-tumour vaccines—adjuvant to boost specific immune responses in conjunction with a vaccine designed to generate a particular anti-tumour immune response.

Enhancement of immune responses against pathogens include bacteria, viruses and parasites either with or without vaccination.

Post-infection vaccination—to boost anti-viral immune responses after infection.

Figure 4:
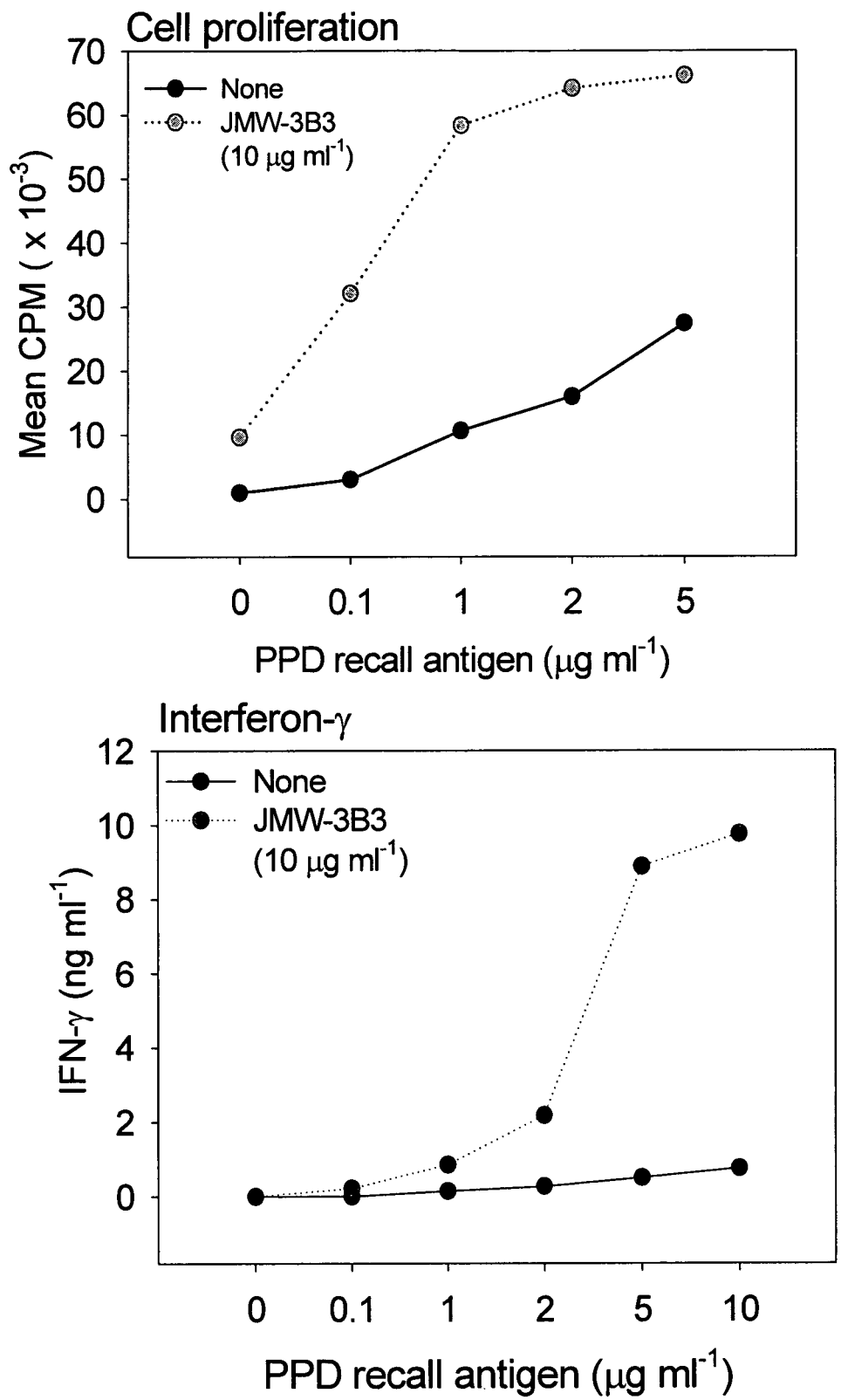
Figure 4:
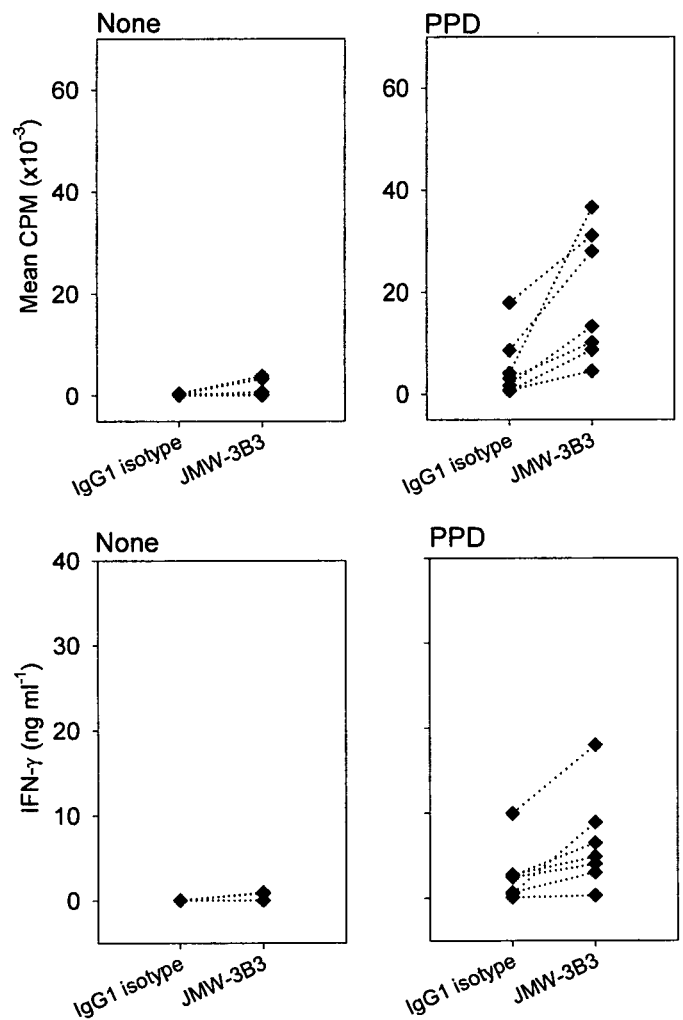

As described below, the enhancement or stimulation of the antigen-specific immune response can be selective in the sense that in the absence of antigen, the enhancement or stimulation of the immune system is mild or absent (compare '0' μg/ml antigen in the presence or absence of antibody in FIG. 4).

Those skilled in the art will appreciate that, in the light of the disclosure herein, there will be many indications or diseases in which blockade of sCTLA-4 action can be used to advantageous effect to enhance a specific immune response.

By way of non-limiting example, in the treatment of cancer or other proliferative disease, an immunogenic tumour could be targeted with e.g. in melanoma, renal carcinoma, lymphoma, fibrosarcoma, colon carcinoma, prostate and ovarian cancer (50-55).

In infection, blockade of sCTLA4 may have utility in enhancing effective immune responses against HIV (35, 36), nematode and *Leishmania* infection (32,33), and also pneumonococcus capsular polysaccharides (34).

It will be appreciated that antibody molecules of the present invention can be used in combination with other immune enhancing moieties e.g., GM-CSF, interleukin (IL-) 2, or other specific vaccines comprising any immunogenic substance from a particular pathogen.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg-1.0 g, and this may be administered as a bolus intravenously. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

A further mode of administration employs precoating of, or otherwise incorporation into, indwelling devices, for which the optimal amount of antibody will be determined by means of appropriate experiments.

A further mode of administration is to deplete plasma of sCTLA-4, which could then replace (for example via plasmapheresis) the patient's own plasma.

A further mode of administration employs precoating of, or otherwise incorporation into, indwelling devices, for which the optimal amount of antibody will be determined by means of appropriate experiments.

Antibody molecules of the present invention will usually be administered in the form of a pharmaceutical composition, which may comprise at least one component in addition to the antibody molecule.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, ibuprofen or ketoprofen) or opiates such as morphine, or anti-emetics.

The antibody molecules of the present invention have utility in dissecting out the individual regulatory function pertaining to both full length cell surface CTLA-4 and the sCTLA-4 alternative isoform.

Antibody molecules according to the invention may be used in a method of detection, for example, to determine the concentration or presence of sCTLA4 in the body, or in a cell or tissue.

The present invention provides a method comprising causing or allowing binding of an antibody molecule as provided herein to sCTLA-4. As noted, such binding may take place in vivo, e.g. following administration of an antibody molecule, or nucleic acid encoding an antibody molecule, or it may take place in vitro, for example in ELISA, Western blotting, immunocytochemistry, immuno-precipitation, affinity chromatography, flow cytometry or so on.

The amount of binding of antibody molecule to sCTLA-4 may be determined. Quantitation may be related to the amount of the sCTLA-4 in a test sample, which may be of diagnostic interest e.g. of diseases or indications associated with high or low serum levels of sCTLA-4. Such methods may be performed in vitro, for example, on samples previously obtained from the individual concerned.

Currently, there are several reports in the scientific literature reporting that increased levels of sCTLA-4 can be detected in patients with disease, including several autoimmune diseases, e.g., autoimmune thyroid disease, scleroderma, active systemic lupus erythematosus (42-48). Soluble CTLA-4 has also been reportedly detected in patients with asthma (49). The use of an antibody molecule selective for sCTLA-4 may thus have utility in investigating and, if appropriate, diagnosing or assessing any of these diseases or indications, or any others associated with high or low serum levels of sCTLA-4.

The reactivities of antibodies on a sample may be determined by any appropriate means. Radioimmunoassay (RIA) is one possibility. Radioactive labelled sCTLA-4 is mixed with unlabelled sCTLA-4 (the test sample) and allowed to bind to the antibody. Bound sCTLA-4 is physically separated from unbound sCTLA-4 and the amount of radioactive sCTLA-4 bound to the antibody determined. The more sCTLA-4 there is in the test sample the less radioactive sCTLA-4 will bind to the antibody. A competitive binding assay may also be used with non-radioactive sCTLA-4, using sCTLA-4 or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of an antibody molecule as above for measuring sCTLA-4 levels in a competition assay, that is to say a method of measuring the level of sCTLA-4 in a sample by employing an antibody molecule as provided by the present invention in a competition assay. This may be where the physical separation of bound from unbound sCTLA-4 is not required. Linking a reporter molecule to the antibody molecule so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of sCTLA-4 directly, by employing an antibody molecule according to the invention for example in a biosensor system.

Antibody molecules according to the invention also have utility as research tools in a variety of contexts. By way of non-limiting example they may be used to measure relative amounts of sCTLA-4 in a sample. The molecules can be used to detect the presence of sCTLA-4 in cells, serum, plasma, or cell culture supernatants utilising a number of techniques. When conjugated to fluorescent labels (e.g., phycoerythrin) the molecules can detect sCTLA-4 in cells, e.g., T cells by flow cytometry or fluorescent microscopy. ELISA can be used to detect the presence of sCTLA-4 in fluids including serum. The antibody molecules can also be used to adsorb and purify sCTLA-4 from fluids using affinity chromatography. Additionally, they may be used to investigate the function of sCTLA-4 in vitro by adding it to purified peripheral blood mononuclear cells or purified cell subsets (e.g., T cells) in the presence of activating factors.

The mode of determining binding in any of these applications is not per se a feature of the present invention and those skilled in the art are able to choose a suitable mode according to their preference and general knowledge.

Terminology

Antibody Molecule

The terms "Antibody molecule" as used herein is understood to refer to molecules or active fragments of molecules that bind to known antigens, particularly to refer to immunoglobulin molecules and to immunologically active portions of immunoglobulin molecules, i.e. molecules that contain a binding site that immunospecifically binds an antigen. An immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

Antibodies molecules may be natural or partly or wholly synthetically produced.

Antibodies that are intended to be within the scope of the present invention include monoclonal, polyclonal, chimeric, single chain, bispecific or bi-effective, simianized, human and humanized antibodies as well as active fragments thereof. Examples of active fragments of molecules that bind to known antigens include (which comprise an antigen binding domain) include Fab, F(ab')$_2$, scFv, Fv, and the products of an Fab immunoglobulin expression library, and epitope-binding fragments of any of the antibodies and fragments, plus also dAb, Fd; diabodies and so on.

Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90, 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against sCTLA-4, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996).

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Antigen Binding Domain

Where used herein this describes the part of an antibody molecule which comprises the area which specifically binds to and is complementary to part or all of an antigen. Where an antigen is large, an antibody may only bind to a particular part of the antigen, which part is termed an epitope.

"Specific binding" in this context will be understood to relate to binding arising from a specific interaction between the conformation of an antigen binding domain and its binding partner, as opposed to non-specific binding arising only from van der Waals forces or other non-specific protein:protein interactions.

CDR

The term "CDR" refers to the hypervariable region of an antibody. The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions are based on sequence variability and are the most commonly used (Kabat et al., Sequences of Proteins of Immunological Interest, 5th Ed. Public Health Service, National Institutes of Health, Bethesda, Md. (1991)).

The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes.

Variable domains employed in the invention may be obtained from any germ-line or rearranged human variable domain, or may be a synthetic variable domain based on consensus sequences of known human variable domains. A CDR sequence of the invention (e.g. CDR3) may be introduced into a repertoire of variable domains lacking a CDR (e.g. CDR3), using recombinant DNA technology.

A further alternative is to generate novel VH or VL regions carrying a CDR-derived sequences of the invention using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR.

Humanized Antibody

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl. Acad Sci USA, 86:10029-10032 (1989), Hodgson et al., Bio/Technology, 9:421 (1991)).

A "humanized antibody" may also be obtained by a novel genetic engineering approach that enables production of affinity-matured humanlike polyclonal antibodies in large animals such as, for example, rabbits (see, e.g. U.S. Pat. No. 7,129,084).

Monoclonal Antibody

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

Functionally Equivalent Antibody

"Functionally equivalent antibody" is understood within the scope of the present invention to refer to an antibody which substantially shares at least one major functional property with JMW-3B3, for example functional properties herein described including, but not limited to: binding specificity to sCTLA-4.

Immunogen and Antigen

An "immunogen" is defined as any substance that can induce an adaptive immune response whereas an "antigen" is any substance that can be recognised (in terms of an immune response) by the cells of the adaptive immune system.

Comprise

This is generally used in the sense of "include", that is to say permitting the presence of one or more features or components.

Isolated

This refers to the state in which antibody molecules of the invention, or nucleic acid encoding such antibody molecules, will generally be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Antibody molecules may be glycosylated, either naturally or by systems of heterologous eukaryotic cells (e.g. CHO or NS0 (ECACC 85110503) cells, or they may be (for example if produced by expression in a prokaryotic cell) unglycosylated.

Variant Sequences

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for example 95% identity with a reference sequence of the present invention, the parameters are preferably adjusted so that the percentage of identity is calculated over the entire length of the reference sequence and homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

As used herein a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject epitope. One of ordinary skill in the art will be able to predict which amino acid substitutions can be made while maintaining a high probability of being conformationally and antigenically neutral. Such guidance is provided, for example in Berzofsky, (1985) Science 229:932-940 and Bowie et al. (1990) Science 247:1306-1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physiochemically similar, amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to micro-complement fixation methods (see, e.g. Wasserman et al. (1961) J. Immunol. 87:290-295; Levine et al. (1967) Meth. Enzymol. 11:928-936) and through binding studies using conformation-dependent monoclonal antibodies (see, e.g. Lewis et al. (1983) Biochem. 22:948-954).

All the above described techniques are known as such in the art and in themselves do not form part of the present invention. The skilled person will be able to use such techniques to provide antibody molecules of the invention using routine methodology in the art.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

Sequences

SEQ ID NO: 1 JMW-3B3 VL encoding nucleotide sequence

SEQ ID NO: 2 JMW-3B3 VL amino acid sequence

SEQ ID NO: 3 JMW-3B3 VH encoding nucleotide sequence

SEQ ID NO: 4 JMW-3B3 VH amino acid sequence

SEQ ID NO: 5 JMW-3B3 VH CDR1, within VH amino acid sequence (SEQ ID NO: 4)

SEQ ID NO: 6 JMW-3B3 VH CDR2, within VH amino acid sequence (SEQ ID NO: 4)

SEQ ID NO: 7 JMW-3B3 VH CDR3, within VH amino acid sequence (SEQ ID NO: 4)

SEQ ID NO: 8 JMW-3B3 VL CDR1, within VL amino acid sequence (SEQ ID NO: 2)

SEQ ID NO: 9 JMW-3B3 VL CDR2, within VL amino acid sequence (SEQ ID NO: 2)

SEQ ID NO: 10 JMW-3B3 VL CDR3, within VL amino, acid sequence (SEQ ID NO: 2)

SEQ ID NO: 11 sCTLA4 C-terminal protein sequence ($A_{116}$-$M_{137}$)

The above sequences are all shown within FIGS. 1 and 2. The hypervariable complementarity determining regions (CDRs), which make up the antigen binding site, are delineated with arrows.

FIGURES

FIG. 1. Annotated nucleotide and amino acid sequence of the variable light chain framework and complementary determining regions of monoclonal anti-sCTLA-4 antibody, JMW-3B3.

FIG. 2. Annotated nucleotide and amino acid sequence of the variable heavy chain framework and complementary determining regions of monoclonal anti-sCTLA-4 antibody, JMW-3B3.

Figure 3:
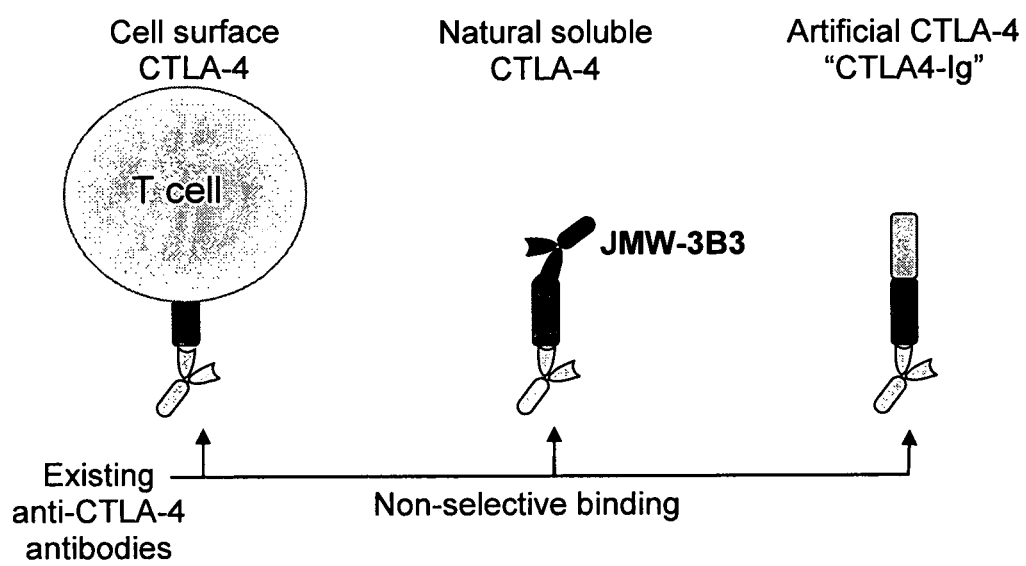

FIG. 3. Existing antibodies bind all the major forms of CTLA-4—both CTLA-4 on the surfaces of lymphocytes, e.g., CD4$^+$ T cells, and natural soluble CTLA-4. JMW3B3 only binds the natural soluble form of human CTLA-4 targeting a protein sequence carried only by the soluble form. Note, sometimes an artificial recombinant form of CTLA-4 (CTLA4-Ig) is sometimes referred to in the literature as soluble CTLA-4. JMW-3B3 does not bind that form either.

FIG. 4.

(a) Monoclonal antibody, JMW-3B3, specific for human soluble CTLA-4 enhances antigen-specific immune responses. Peripheral blood mononuclear cells (1 million per well, 1 ml culture medium) were incubated with increasing amounts of purified protein derivative of *Mycobacterium tuberculosis* (PPD) for 5 days at 37° C., 5% $CO_2$, in the presence or absence of JMW-3B3. The graphs show that addition of the antibody, enhanced both immune cell proliferation (top panel) and increased production of the effector cytokine, interferon-γ.

(b) Enhancement of antigen-specific immune responses by anti-sCTLA-4 monoclonal antibody, JMW-3B3. Data from six separate experiments demonstrating differences in IFN-γ and cell proliferation when PBMC were stimulated with either 0 or 5 μg ml$^{-1}$ PPD recall antigen in the presence of anti-sCTLA-4 mAb, JMW-3B3 or an IgG1 isotype control.

FIG. 5. ELISA to compare detection of CTLA-4 by a pan-specific anti-CTLA-4 antibody with soluble CTLA-4 selective antibody JMW-3B3. A common pan-specific anti-CTLA-4 antibody was used to capture CTLA-4 present in 11 healthy volunteer donor sera. Plates were blocked with 2% skimmed milk product in phosphate buffered saline. Presence of CTLA-4 was detected either with a biotinylated pan-specific anti-CTLA-4 antibody or biotinylated sCTLA-4 selective antibody, JMW-3B3. Streptavidin-conjugated alkaline phosphatase was then used to detect presence of bound biotinylated antibody in each case. Plates were developed using a common phosphatase substrate and a spectrophotometer with a 405 nm filter used to detect colour change.

Figure 6:
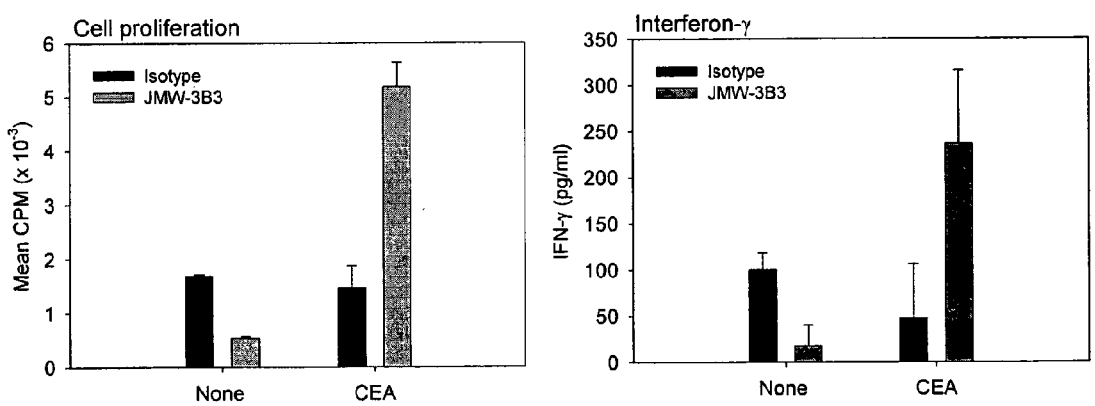

FIG. 6. Enhancement of tumour associated carcinoembryonic antigen (CEA) specific immune responses by anti-sCTLA-4 monoclonal antibody, JMW-3B3. PBMC were stimulated with either 0 or 10 μg ml$^{-1}$ CEA antigen in the presence of anti-sCTLA-4 mAb, JMW-3B3 or an IgG1 isotype control (None).

Figure 7:
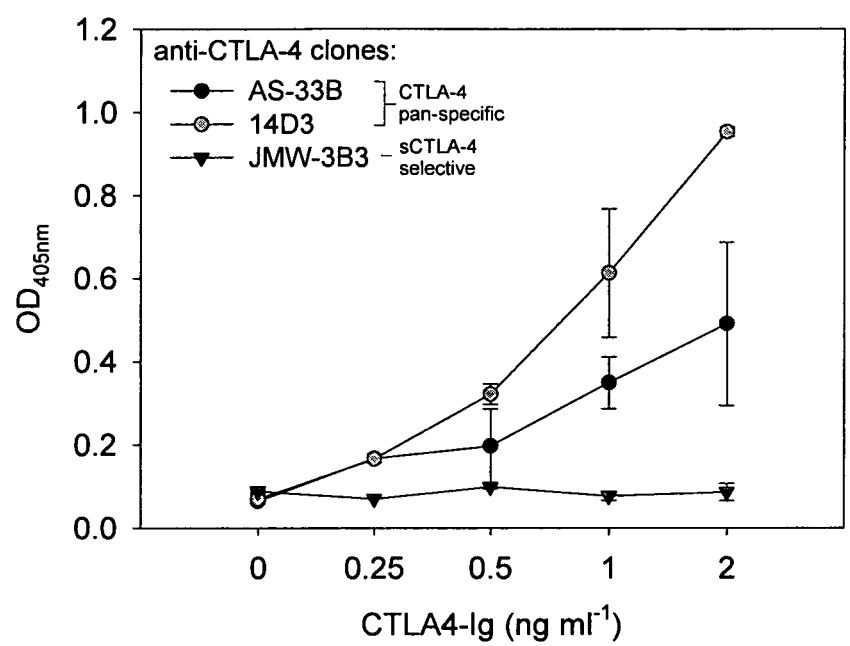

FIG. 7. Anti-sCTLA-4 JMW-3B3 distinguishes, in sera and culture supernatant, true natural soluble CTLA-4 from extracellular membrane-bound CTLA-4 (mCTLA-4). The extracellular portion of mCTLA-4 is encoded by exon 2 and is identical in sCTLA-4, mCTLA-4 and the recombinant soluble form of CTLA-4, CTLA4-Ig. As JMW-3B3 was raised against the unique C-terminal region of sCTLA-4 it does not cross-react the extracellular CTLA-4 domain. Two biotinylated pan-specific anti-CTLA-4 detection mAbs (clones AS-33 and 14D3), specific for the extracellular domain of CTLA-4, were compared for their ability to bind CTLA4 with the JMW-3B3 in a typical sandwich ELISA. Pan-specific anti-CTLA-4 mAb (clone BNI3) was used as the capture antibody.

EXAMPLES

Experimental

JMW-3B3 is a mouse IgG1λ mAb specific for human sCTLA-4 (see FIGS. 1 and 2).

FIG. 3 provides a non-technical illustration of how JMW-3B3 mAb differs from current pan-specific anti-CTLA-4 antibodies.

The JMW-3B3 mAb was raised against and recognises an epitope existing within the C terminal region of sCTLA-4.

Balb/c mice were immunised with a peptide representing the c-terminus of human sCTLA-4 conjugated to a carrier protein, Keyhole Limpet haemocyanin (KLH). Mice were immunised subcutaneously twice with a three week interval. The first immunisation comprised peptide-KLH (1 mg/ml) suspended in an emulsion of Complete Freund's Adjuvant. The subsequent immunisation was of the same peptide-KLH concentration but applied in a suspension of Incomplete Freund's Adjuvant. A week prior to sacrifice, mice were injected intraperitoneally with peptide-KLH in a sterile saline solution. Preparation, selection and maintenance of hybridomas from splenic B cells was performed using standard protocols that are widely available. The immortal cell line fusion partner was SP2/0-Ag14 from the Health Protection Agency Culture Collection, Salisbury, UK (ECACC). Detection of putative anti-sCTLA-4 antibody producing hybridomas was performed using a peptide ELISA developed in the laboratory. Peptide representing the C terminal sequence of human soluble CTLA-4 was coated on Greiner 3912 flexible 96 well ELISA plates at 50 µg/ml in water overnight at 37° C. The peptide solution evaporated completely during this period and plates were then washed with phosphate buffered saline (PBS) twice and blocked with 2% Marvel in PBS for an hour at 36° C. Sampled supernatants from hybridoma cell cultures (about 100 actively growing hybridomas) were incubated on the plates before detection with an anti-mouse IgG Fc specific reagent conjugated to alkaline phosphatase. Plates were developed with a phosphatase substrate and positive wells detected by an increase in absorbance at 405 nm. Hybridomas positive for sCTLA-4 peptide were stored under liquid nitrogen. Hybridoma JMW-3B3 was cloned twice using typical limiting dilution protocols and its ability to bind native sCTLA-4 molecule was tested using sCTLA-4 purified from serum.

Addition of the antibody to cell cultures of normal donor peripheral blood mononuclear cells (PBMC) enhances antigen-specific immune responses. Notably, the stimulatory effects of the antibody in the absence of an antigenic stimulus are mild to absent. FIG. 4(a) shows an example of the stimulatory activity of JMW-3B3. PBMC from a healthy donor were incubated in vitro in the presence of increasing amounts of purified protein derivative of *Mycobacterium tuberculosis* (PPD) recall antigen, in the presence or absence of 10 µg/ml JMW-3B3. In the presence of JMW-3B3 the PPD-specific immune response is enhanced both in terms of increased cell proliferation and the production of the effector cytokine, interferon-γ. FIG. 4(b) shows the results of further investigations using PPD.

Interestingly, enhancement of the immune response relied upon the presence of antigen. In effect, antibody blockade of sCTLA-4 had highly selective positive effects on the immune system. Experiments demonstrating this enhancement were repeated at least four times with the same conclusion.

FIG. 6 shows enhancement of the immune response against CEA in the presence of JMW-3B3 and a control.

In another experiment, sera from 11 normal donors was tested for the presence of sCTLA-4. A capture ELISA technique was used in which JMW-3B3 was compared with a commonly used pan-specific anti-human CTLA-4 antibody (FIG. 5). In this case, two positive samples were both identified by each antibody, but the pan-specific anti-CTLA-4 antibody identified a further three positive samples. These do not carry the sCTLA-4 epitope and are therefore likely to be either degraded sCTLA-4 or CTLA-4 cleaved from the surface membrane. This demonstrates the selective nature of the JMW-3B3 antibody in identifying functional sCTLA-4; this is also demonstrated in FIG. 7.

REFERENCES (1) Jenkins M K, Taylor P S, Norton S D, Urdahl K B. CD28 delivers a costimulatory signal involved in antigen-specific IL-2 production by human T cells. J. Immunol. 1991 Oct. 15; 147(8):2461-2466.
(2) Norton S D, Zuckerman L, Urdahl K B, Shefner R, Miller J, Jenkins M K. The CD28 ligand, B7, enhances IL-2 production by providing a costimulatory signal to T cells. J. Immunol. 1992 Sep. 1; 149(5):1556-1561.
(3) Harding F A, McArthur J G, Gross J A, Raulet D H, Allison J P. CD28-mediated signalling co-stimulates murine T cells and prevents induction of anergy in T-cell clones. Nature 1992 Apr. 16; 356(6370):607-609.
(4) Linsley P S, Brady W, Grosmaire L, Aruffo A, Damle N K, Ledbetter J A. Binding of the B cell activation antigen B7 to CD28 costimulates T cell proliferation and interleukin 2 mRNA accumulation. J. Exp. Med. 1991 Mar. 1; 173(3): 721-730.
(5) Hathcock K S, Laszlo G, Dickler H B, Bradshaw J, Linsley P, Hodes R J. Identification of an alternative CTLA-4 ligand costimulatory for T cell activation. Science 1993 Nov. 5; 262(5135):905-907.
(6) Brunet J F, Denizot F, Luciani M F, Roux-Dosseto M, Suzan M, Mattei M G, et al. A new member of the immunoglobulin superfamily—CTLA-4. Nature 1987 Jul. 16-22; 328(6127):267-270.
(7) Dariavach P, Mattei M G, Golstein P, Lefranc M P. Human Ig superfamily CTLA-4 gene: chromosomal localization and identity of protein sequence between murine and human CTLA-4 cytoplasmic domains. Eur. J. Immunol. 1988 December; 18(12):1901-1905.
(8) Linsley P S, Brady W, Urnes M, Grosmaire L S, Damle N K, Ledbetter J A. CTLA-4 is a second receptor for the B cell activation antigen B7. J. Exp. Med. 1991 Sep. 1; 174 (3):561-569.
(9) Walunas T L, Lenschow D J, Bakker C Y, Linsley P S, Freeman G J, Green J M, et al. CTLA-4 can function as a negative regulator of T cell activation. Immunity 1994 August; 1(5):405-413.
(10) Krummel M F, Allison J P. CD28 and CTLA-4 have opposing effects on the response of T cells to stimulation. J. Exp. Med. 1995 Aug. 1; 182(2):459-465.
(11) Heikkinen J, Mottonen M, Alanen A, Lassila O. Phenotypic characterization of regulatory T cells in the human decidua. Clin. Exp. Immunol. 2004 May; 136(2):373-378.
(12) Jago C B, Yates J, Camara N O, Lechler R I, Lombardi G. Differential expression of CTLA-4 among T cell subsets. Clin. Exp. Immunol. 2004 June; 136(3):463-471.
(13) Birebent B, Lorho R, Lechartier H, de Guibert S, Alizadeh M, Vu N, et al. Suppressive properties of human CD4+ CD25+ regulatory T cells are dependent on CTLA-4 expression. Eur. J. Immunol. 2004 December; 34(12): 3485-3496.
(14) Read S, Malmstrom V, Powrie F. Cytotoxic T lymphocyte-associated antigen 4 plays an essential role in the function of CD25(+)CD4(+) regulatory cells that control intestinal inflammation. J. Exp. Med. 2000 Jul. 17; 192(2): 295-302.
(15) Takahashi T, Tagami T, Yamazaki S, Uede T, Shimizu J, Sakaguchi N, et al. Immunologic self-tolerance maintained by CD25(+)CD4(+) regulatory T cells constitutively expressing cytotoxic T lymphocyte-associated antigen 4. J. Exp. Med. 2000 Jul. 17; 192(2):303-310.
(16) Kingsley C I, Karim M, Bushell A R, Wood K J. CD25+ CD4+ regulatory T cells prevent graft rejection: CTLA-4- and IL-10-dependent immunoregulation of alloresponses. J. Immunol. 2002 Feb. 1; 168(3):1080-1086.
(17) Manzotti C N, Tipping H, Perry L C, Mead K I, Blair P J, Zheng Y, et al. Inhibition of human T cell proliferation by CTLA-4 utilizes CD80 and requires CD25+ regulatory T cells. Eur. J. Immunol. 2002 October; 32(10):2888-2896.
(18) Wing K, Onishi Y, Prieto-Martin P, Yamaguchi T, Miyara M, Fehervari Z, et al. CTLA-4 control over Foxp3+ regulatory T cell function. Science 2008 Oct. 10; 322(5899): 271-275.
(19) Tivol E A, Boyd S D, McKeon S, Borriello F, Nickerson P, Strom T B, et al. CTLA4Ig prevents lymphoproliferation and fatal multiorgan tissue destruction in CTLA-4-deficient mice. J. Immunol. 1997 Jun. 1; 158(11):5091-5094.

(20) Waterhouse P, Bachmann M F, Penninger J M, Ohashi P S, Mak T W. Normal thymic selection, normal viability and decreased lymphoproliferation in T cell receptor-transgenic CTLA-4-deficient mice. Eur. J. Immunol. 1997 August; 27(8):1887-1892.

(21) Kearney E R, Walunas T L, Karr R W, Morton P A, Loh D Y, Bluestone J A, et al. Antigen-dependent clonal expansion of a trace population of antigen-specific CD4+ T cells in vivo is dependent on CD28 costimulation and inhibited by CTLA-4. J. Immunol. 1995 Aug. 1; 155(3):1032-1036.

(22) Walunas T L, Bakker C Y, Bluestone J A. CTLA-4 ligation blocks CD28-dependent T cell activation. J. Exp. Med. 1996 Jun. 1; 183(6):2541-2550.

(23) Krummel M F, Allison J P. CTLA-4 engagement inhibits IL-2 accumulation and cell cycle progression upon activation of resting T cells. J. Exp. Med. 1996 Jun. 1; 183(6):2533-2540.

(24) Krummel M F, Sullivan T J, Allison J P. Superantigen responses and co-stimulation: CD28 and CTLA-4 have opposing effects on T cell expansion in vitro and in vivo. Int. Immunol. 1996 April; 8(4):519-523.

(25) Leach D R, Krummel M F, Allison J P. Enhancement of antitumor immunity by CTLA-4 blockade. Science 1996 Mar. 22; 271(5256):1734-1736.

(26) Kwon E D, Hurwitz A A, Foster B A, Madias C, Feldhaus A L, Greenberg N M, et al. Manipulation of T cell costimulatory and inhibitory signals for immunotherapy of prostate cancer. Proc. Natl. Acad. Sci. U.S.A. 1997 Jul. 22; 94(15):8099-8103.

(27) Yang Y F, Zou J P, Mu J, Wijesuriya R, Ono S, Walunas T, et al. Enhanced induction of antitumor T-cell responses by cytotoxic T lymphocyte-associated molecule-4 blockade: the effect is manifested only at the restricted tumor-bearing stages. Cancer Res. 1997 Sep. 15; 57(18):4036-4041.

(28) Hurwitz A A, Yu T F, Leach D R, Allison J P. CTLA-4 blockade synergizes with tumor-derived granulocyte-macrophage colony-stimulating factor for treatment of an experimental mammary carcinoma. Proc. Natl. Acad. Sci. U.S.A. 1998 Aug. 18; 95(17):10067-10071.

(29) Mokyr M B, Kalinichenko T, Gorelik L, Bluestone J A. Realization of the therapeutic potential of CTLA-4 blockade in low-dose chemotherapy-treated tumor-bearing mice. Cancer Res. 1998 Dec. 1; 58(23):5301-5304.

(30) Phan G Q, Yang J C, Sherry R M, Hwu P, Topalian S L, Schwartzentruber D J, et al. Cancer regression and autoimmunity induced by cytotoxic T lymphocyte-associated antigen 4 blockade in patients with metastatic melanoma. Proc. Natl. Acad. Sci. U.S.A. 2003 Jul. 8; 100(14):8372-8377.

(31) Fong L, Small E J. Anti-cytotoxic T-lymphocyte antigen-4 antibody: the first in an emerging class of immunomodulatory antibodies for cancer treatment. J. Clin. Oncol. 2008 Nov. 10; 26(32):5275-5283.

(32) McCoy K, Camberis M, Gros G L. Protective immunity to nematode infection is induced by CTLA-4 blockade. J. Exp. Med. 1997 Jul. 21; 186(2):183-187.

(33) Saha B, Chattopadhyay S, Germond R, Harlan D M, Perrin P J. CTLA4 (CD152) modulates the Th subset response and alters the course of experimental *Leishmania major* infection. Eur. J. Immunol. 1998 December; 28(12):4213-4220.

(34) Boudewijns M, Jeurissen A, Wuyts M, Moens L, Boon L, Van Neerven J J, et al. Blockade of CTLA-4 (CD152) enhances the murine antibody response to pneumococcal capsular polysaccharides. J. Leukoc. Biol. 2005 November; 78(5):1060-1069.

(35) Hryniewicz A, Boasso A, Edghill-Smith Y, Vaccari M, Fuchs D, Venzon D, et al. CTLA-4 blockade decreases TGF-beta, IDO, and viral RNA expression in tissues of SIVmac251-infected macaques. Blood 2006 Dec. 1; 108 (12):3834-3842.

(36) Kaufmann D E, Kavanagh D G, Pereyra F, Zaunders J J, Mackey E W, Miura T, et al. Upregulation of CTLA-4 by HIV-specific CD4+ T cells correlates with disease progression and defines a reversible immune dysfunction. Nat. Immunol. 2007 November; 8(11):1246-1254.

(37) Karandikar N J, Vanderlugt C L, Walunas T L, Miller S D, Bluestone J A. CTLA-4: a negative regulator of autoimmune disease. J. Exp. Med. 1996 Aug. 1; 184(2):783-788.

(38) Teft W A, Kirchhof M G, Madrenas J. A molecular perspective of CTLA-4 function. Annu. Rev. Immunol. 2006; 24:65-97.

(39) Magistrelli G, Jeannin P, Herbault N, Benoit De Coignac A, Gauchat J F, Bonnefoy J Y, et al. A soluble form of CTLA-4 generated by alternative splicing is expressed by nonstimulated human T cells. Eur. J. Immunol. 1999 November; 29(111:3596-3602.

(40) Oaks M K, Hallett K M, Penwell R T, Stauber E C, Warren S J, Tector A J. A native soluble form of CTLA-4. Cell. Immunol. 2000 May 1; 201(2):144-153.

(41) Ueda H, Howson J M, Esposito L, Heward J, Snook H, Chamberlain G, et al. Association of the T-cell regulatory gene CTLA4 with susceptibility to autoimmune disease. Nature 2003 May 29; 423(6939):506-511.

(42) Collins, A. V., D. W. Brodie, R. J. Gilbert, A. Iaboni, R. Manso-Sancho, B. Walse, D. I. Stuart, P. A. van der Merwe, and S. J. Davis. The interaction properties of costimulatory molecules revisited. Immunity 2002.17:201-210.

(43) Oaks, M. K., and K. M. Hallett. Cutting edge: a soluble form of CTLA-4 in patients with autoimmune thyroid disease. J. Immunol. 2000.164:5015-5018.

(44) Liu, M. F., C. R. Wang, P. C. Chen, and L. L. Fung. Increased expression of soluble cytotoxic T-lymphocyte-associated antigen-4 molecule in patients with systemic lupus erythematosus. Scand. J. Immunol. 2003.57:568-572.

(45) Sato, S., M. Fujimoto, M. Hasegawa, K. Komura, K. Yanaba, I. Hayakawa, T. Matsushita, and K. Takehara. Serum soluble CTLA-4 levels are increased in diffuse cutaneous systemic sclerosis. Rheumatology (Oxford) 2004.43:1261-1266.

(46) Wong, C. K., S. W. Lun, F. W. Ko, W. K. Ip, D. S. Hui, and C. W. Lam. Increased expression of plasma and cell surface co-stimulatory molecules CTLA-4, CD28 and CD86 in adult patients with allergic asthma. Clin. Exp. Immunol. 2005.141:122-129.

(47) Wong, C. K., L. C. Lit, L. S. Tam, E. K. L1, and C. W. Lam. Aberrant production of soluble costimulatory molecules CTLA-4, CD28, CD80 and CD86 in patients with systemic lupus erythematosus. Rheumatology (Oxford) 2005. 44:989-994.

(48) Saverino, D., R. Brizzolara, R. Simone, A. Chiappori, F. Milintenda-Floriani, G. Pesce, and M. Bagnasco. Soluble CTLA-4 in autoimmune thyroid diseases: relationship with clinical status and possible role in the immune response dysregulation. 2007. Clin. Immunol. 123:190-198.

(49) Ip, W. K., C. K. Wong, T. F. Leung, and C. W. Lam. Plasma concentrations of soluble CTLA-4, CD28, CD80 and CD86 costimulatory molecules reflect disease severity of acute asthma in children. 2006. Pediatr. Pulmonol. 41:674-682.
(50) Hodi F S, Mihm M C, Soiffer R J, et al. Biologic activity of cytotoxic T lymphocyte-associated antigen 4 antibody blockade in previously vaccinated metastatic melanoma and ovarian carcinoma patients. Proc Natl Acad Sci USA. 2003; 100:4712-4717.
(51) Attia P, Phan G Q, Maker A V, et al. Autoimmunity correlates with tumor regression in patients with metastatic melanoma treated with anti-cytotoxic T-lymphocyte antigen-4. J Clin Oncol. 2005; 23:6043-6053.
(52) Small E J, Tchekmedyian N S, Rini B I, Fong L, Lowy I, Allison J P. A pilot trial of CTLA-4 blockade with human anti-CTLA-4 in patients with hormone-refractory prostate cancer. Clin Cancer Res. 2007; 13:1810-1815.
(53) Phan G Q, Yang J C, Sherry R M, et al. Cancer regression and autoimmunity induced by cytotoxic T lymphocyte-associated antigen 4 blockade in patients with metastatic melanoma. Proc Natl Acad Sci USA. 2003; 100:8372-8377.
(54) Korman A, Yellin M, Keler T. Tumor immunotherapy: preclinical and clinical activity of anti-CTLA4 antibodies. Curr Opin Investig Drugs. 2005; 6:582-591.
(55) Wolchok J D and Saenger Y. The mechanism of anti-CTLA-4 activity and the negative regulation of T-cell activation. Oncologist. 2008; 13 Suppl 4:2-9.

The invention claimed is:

1. An antibody molecule which is A monoclonal antibody, or a fragment or antigen binding domain thereof, which binds specifically to a native soluble form of cytotoxic T-lymphocyte antigen 4 (sCTLA-4) and which does not specifically bind to cytotoxic T-lymphocyte antigen 4 (CTLA-4) on the surfaces of lymphocytes, wherein the antibody molecule specifically binds an sCTLA-4 epitope within the amino acid sequence AKEKKPSYNRGLCENAPNRARM (SEQ ID NO: 11) and wherein the antibody molecule comprises:

(i) a VH domain comprising an amino acid sequence that is identical to SEQ ID NO: 4 and, (ii) a VL domain comprising an amino acid sequence that is identical to SEQ ID NO: 2.

2. An antibody molecule which is a monoclonal antibody, or a fragment or antigen binding domain thereof, which binds specifically to a native soluble form cytotoxic T-lymphocyte antigen 4 (sCTLA-4) and which does not specifically bind to cytotoxic T-lymphocyte antigen 4 (CTLA-4) on the surfaces of lymphocytes, wherein the antibody molecule specifically binds an sCTLA-4 epitope within the amino acid sequence AKEKKPSYNRGLCENAPNRARM (SEQ ID NO: 11) and wherein the antibody molecule comprises:

(i) an antibody VH domain comprising three VH CDRs with the amino acid sequences of SEQ ID NO: 7, SEQ ID NO: 5 and SEQ ID NO: 6; and (ii) an antibody VL domain comprising three VL CDRs with the amino acid sequences of SEQ ID NO: 8, SEQ ID NO: 9 and SEQ ID NO: 10.

3. An antibody molecule according to claim 2 comprising the JMW-3B3 VH domain (SEQ ID NO: 4).

4. An antibody molecule according to claim 3 comprising the JMW-3B3 VL domain (SEQ ID NO: 2).

5. An antibody molecule according to claim 1 which competes for binding to sCTLA-4 with an sCTLA-4 binding domain of an antibody comprising the JMW-3B3 VH domain (SEQ ID NO: 4) and the JMW-3B3 VL domain (SEQ ID NO: 2).

6. An antibody molecule according to claim 1 or claim 6 which is capable of enhancing antigen-specific T lymphocytic cell responses.

7. An antibody molecule according to claim 1 that comprises, consists of or consists essentially of an antibody fragment or an antigen binding domain and is selected from: Fab, scFv, Fv, and F(ab')$_2$.

8. An antibody molecule according to claim 1 that comprises an antibody constant region.

9. An antibody molecule according to claim 8 that is a whole antibody.

10. An antibody molecule according to claim 9 that is a humanized antibody.

11. A VH domain comprising an amino acid sequence that is 99% identical to SEQ ID NO: 4, wherein an antibody comprising said domain binds specifically to a native soluble form of cytotoxic T-lymphocyte antigen 4 (sCTLA-4) and does not specifically bind to cytotoxic T-lymphocyte antigen 4 (CTLA-4) on the surfaces of lymphocytes, and wherein the VH domain specifically binds an sCTLA-4 epitope within the amino acid sequence AKEKKPSYNRGLCENAPNRARM (SEQ ID NO: 11).

12. A VL domain comprising an amino acid sequence that is 99% identical to SEQ ID NO: 2, wherein an antibody comprising said VL domain bind specifically to a native soluble form of cytotoxic T-lymphocyte antigen 4 (sCTLA-4) and which does not specifically bind to cytotoxic T-lymphocyte antigen 4 (CTLA-4) on the surfaces of lymphocytes, and wherein the VL domain specifically binds an sCTLA-4 epitope within the amino acid sequence AKEKKPSYNR-GLCENAPNRARM (SEQ ID NO: 11).

13. A therapeutic or prophylactic composition comprising an antibody molecule according to claim 1 and a pharmaceutically acceptable carrier, diluent or excipient wherein the antibody molecule is present as an adjuvant and the composition further comprises a further active agent which is an antigen or immunogen.

14. An antibody molecule according to claim 2 that comprises, consists of or consists essentially of an antibody fragment or an antigen binding domain and is selected from: Fab, scFv, Fv, and F(ab')$_2$.

15. An antibody molecule according to claim 2 that comprises an antibody constant region.

16. An antibody molecule according to claim 15 that is a whole antibody.

17. An antibody molecule according to claim 16 that is humanized antibody.

18. A therapeutic or prophylactic composition comprising an antibody molecule according to claim 2 and a pharmaceutically acceptable carrier, diluent or excipient wherein the antibody molecule is present as an adjuvant and the composition further comprises a further active agent which is an antigen or immunogen.

* * * * *

UNITED STATES PATENT AND TRADEMARK OFFICE
CERTIFICATE OF CORRECTION

Page 1 of 1

PATENT NO. : 8,697,845 B2
APPLICATION NO. : 13/203418
DATED : April 15, 2014
INVENTOR(S) : Frank James Ward, Robert Norman Barker and Lekh Nath Dahal It is certified that error appears in the above-identified patent and that said Letters Patent is hereby corrected as shown below:

In the Claims

| Col. No. | Line(s) | Edits |
|---|---|---|
| 31 | 45 | Replace "which is A monoclonal" with --which is a monoclonal-- |
| 32 | 59 | Replace "according to claim 1 or claim 6" with --according to claim 1 or claim 2-- |

Signed and Sealed this
Eighth Day of July, 2014

Michelle K. Lee
*Deputy Director of the United States Patent and Trademark Office*